United States Patent
Kuniyoshi et al.

(10) Patent No.: US 9,423,309 B2
(45) Date of Patent: Aug. 23, 2016

(54) PRESSURE SENSOR, METHOD FOR MANUFACTURE THEREOF, AND PRESSURE DETECTION MODULE

(75) Inventors: Yasuo Kuniyoshi, Tokyo (JP); Yoshiyuki Ohmura, Tokyo (JP); Takashi Sagisaka, Tokyo (JP); Akihiko Nagakubo, Tsukuba (JP); Kazuyuki Ozaki, Tokyo (JP); Taisuke Kimura, Tokyo (JP); Takashige Ohsawa, Tokyo (JP); Masatoshi Nakajima, Tokyo (JP); Masayuki Noguchi, Tokyo (JP); Katsuyoshi Iizuka, Tokyo (JP)

(73) Assignees: Nippon Mektron, Ltd., Minato-Ku (JP); National Institute of Advanced Industrial Science and Technology, Chiyoda-Ku (JP); The University of Tokyo, Bunkyo-Ku (JP)

( * ) Notice: Subject to any disclaimer, the term of this patent is extended or adjusted under 35 U.S.C. 154(b) by 287 days.

(21) Appl. No.: 14/123,126

(22) PCT Filed: Apr. 20, 2012

(86) PCT No.: PCT/JP2012/060738
§ 371 (c)(1),
(2), (4) Date: Jan. 23, 2014

(87) PCT Pub. No.: WO2012/165082
PCT Pub. Date: Dec. 6, 2012

(65) Prior Publication Data
US 2014/0150571 A1    Jun. 5, 2014

(30) Foreign Application Priority Data
May 30, 2011    (JP) .................................. 2011-121090

(51) Int. Cl.
*G01L 1/10* (2006.01)
*G01L 1/20* (2006.01)
(Continued)

(52) U.S. Cl.
CPC . *G01L 1/20* (2013.01); *G01L 1/205* (2013.01); *G01L 5/228* (2013.01); *A61B 5/1036* (2013.01);
(Continued)

(58) Field of Classification Search
CPC ....... G06F 3/044; G06F 3/045; G06F 3/0416; G06F 3/0414; G06F 2203/04105; G01L 1/205; G01L 1/142; G01L 1/146; G01L 1/20; G01L 9/0072
USPC ..................... 324/661; 73/862.625, 715, 718, 73/862.046, 862.626
See application file for complete search history.

(56) References Cited

U.S. PATENT DOCUMENTS

| 6,289,747 B1 * | 9/2001 | Billen .................... H01C 10/12 73/862.046 |
| 6,388,556 B1 | 5/2002 | Imai et al. |

(Continued)

FOREIGN PATENT DOCUMENTS

| JP | 07-44569 U | 11/1995 |
| JP | 10-199368 A1 | 7/1998 |

(Continued)

OTHER PUBLICATIONS

Japanese Office Action (Application No. 2011-121090) dated Feb. 3, 2015 (with English translation).
(Continued)

*Primary Examiner* — Lisa Caputo
*Assistant Examiner* — Jonathan Dunlap

(57) ABSTRACT

A pressure sensor comprising: a base film on which a conductor pattern having one or more electrodes is formed; a cover film laminated on the base film so as to cover the electrodes of the conductor pattern; and a spacer disposed between the cover film and the base film so as to form a hollow portion having a predetermined gap between the electrode and the cover film; wherein a portion corresponding to the hollow portion of the cover film is constructed such that it has a pressure sensing part which is able to deform in a direction to move toward and away from the electrode in accordance with pressure, and of which contact resistance changes in accordance with a contact pressure thereof with the electrode, so that the pressure sensing part detects the pressure by a change of the contact resistance.

2 Claims, 13 Drawing Sheets

(51) Int. Cl.
    *G01L 5/22*     (2006.01)
    *G06F 3/045*     (2006.01)
    *G06F 3/041*     (2006.01)
    *G06F 3/044*     (2006.01)
    *A61B 5/103*     (2006.01)
    *A61B 5/00*     (2006.01)

(52) U.S. Cl.
    CPC ....... *A61B 5/6806* (2013.01); *A61B 2562/0247* (2013.01); *G06F 3/044* (2013.01); *G06F 3/045* (2013.01); *G06F 3/0414* (2013.01); *G06F 3/0416* (2013.01)

(56) References Cited

U.S. PATENT DOCUMENTS

| | | | |
|---|---|---|---|
| 6,392,220 B1* | 5/2002 | Slater | B81B 3/0051 250/216 |
| 6,393,919 B1* | 5/2002 | Ohji | G01L 11/002 73/708 |
| 6,829,942 B2* | 12/2004 | Yanai | A61B 5/113 73/716 |
| 7,038,470 B1* | 5/2006 | Johnson | G01N 33/383 250/390.05 |
| 7,066,030 B2* | 6/2006 | Jacob | G01L 9/0075 73/715 |
| 8,448,530 B2* | 5/2013 | Leuenberger | A61J 1/035 73/760 |
| 2004/0000195 A1 | 1/2004 | Yanai et al. | |
| 2004/0049363 A1 | 3/2004 | Shimizu et al. | |
| 2006/0075831 A1 | 4/2006 | Okuda | |
| 2008/0018608 A1* | 1/2008 | Serban | G06F 3/0416 345/173 |
| 2008/0098820 A1* | 5/2008 | Morsch | G01L 9/0045 73/717 |
| 2009/0013802 A1 | 1/2009 | Orlewski et al. | |
| 2009/0134318 A1 | 5/2009 | Kuniyoshi et al. | |
| 2009/0211352 A1* | 8/2009 | Hatanaka | G01D 11/245 73/146 |
| 2009/0308177 A1* | 12/2009 | Lammerink | G01F 1/6845 73/861.355 |
| 2010/0033354 A1* | 2/2010 | Ejlersen | G06F 3/044 341/33 |
| 2010/0107770 A1* | 5/2010 | Serban | G01L 1/142 73/718 |
| 2010/0242629 A1* | 9/2010 | Leuenberger | A61J 1/035 73/862.625 |
| 2011/0148811 A1* | 6/2011 | Kanehira | G06F 3/044 345/174 |
| 2011/0278078 A1* | 11/2011 | Schediwy | G01L 1/146 178/18.06 |
| 2014/0150571 A1 | 6/2014 | Kuniyoshi et al. | |

FOREIGN PATENT DOCUMENTS

| | | |
|---|---|---|
| JP | 2000-348564 A1 | 12/2000 |
| JP | 2001-056259 A1 | 2/2001 |
| JP | 2001-159569 AI | 6/2001 |
| JP | 2002-131151 A1 | 5/2002 |
| JP | 2002-158103 A1 | 5/2002 |
| JP | 2002-364251 A1 | 12/2002 |
| JP | 2003-248554 A1 | 9/2003 |
| JP | 2003-344195 A1 | 12/2003 |
| JP | 2004-028883 A1 | 1/2004 |
| JP | 2004-323963 A1 | 11/2004 |
| JP | 2006-043843 A1 | 2/2006 |
| JP | 2006-112842 A1 | 4/2006 |
| JP | 2007-078382 A1 | 3/2007 |
| JP | 2012-247372 A1 | 12/2012 |

OTHER PUBLICATIONS

International Search Report dated May 22, 2012.
Japanese Office Action (Application No. 2011-121090) dated Sep. 8, 2015 (with English translation).
Japanese Office Action (Application No. 2011-121090) dated Mar. 8, 2016 (with English translation).
Japanese Office Action (Application No. 2015-078036) dated Mar. 29, 2016 (with English translation).

* cited by examiner

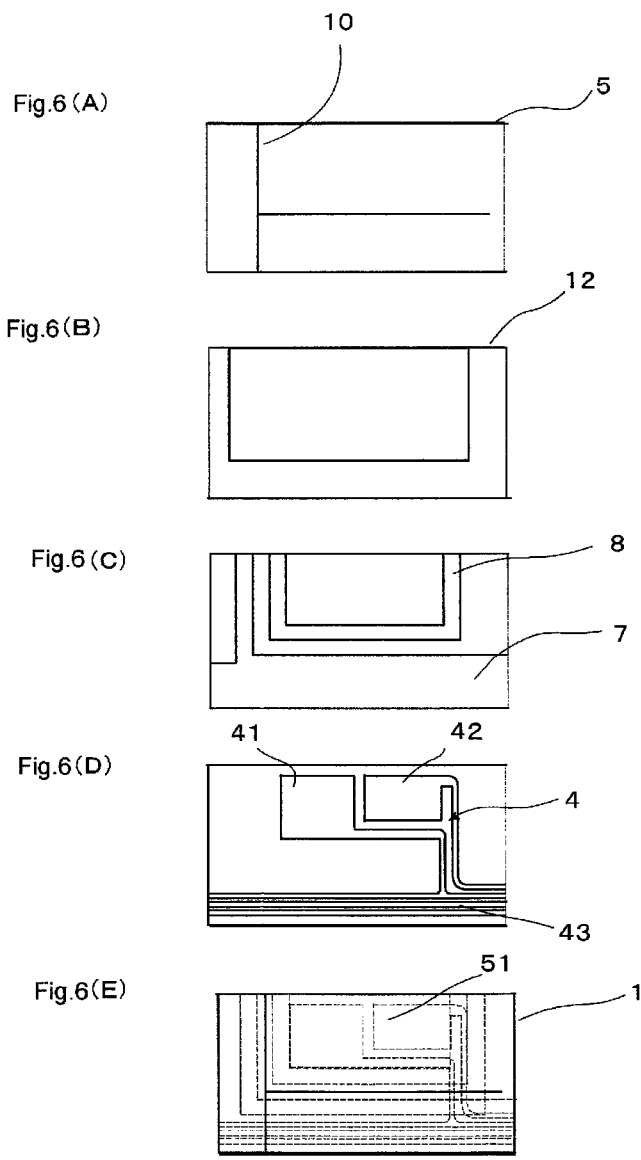

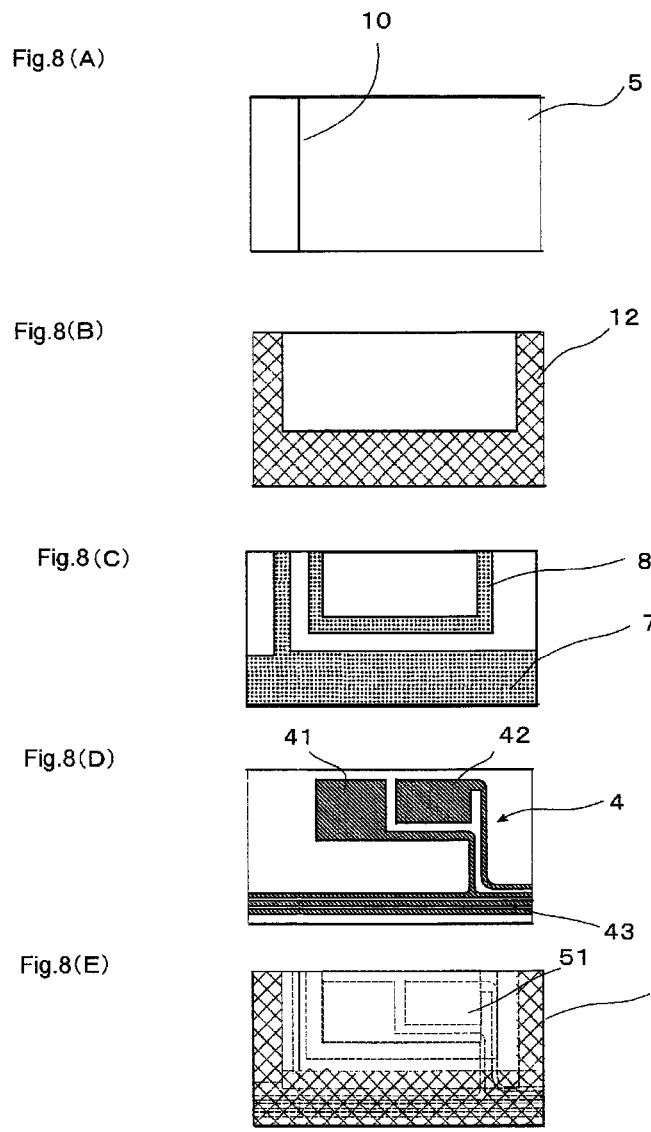

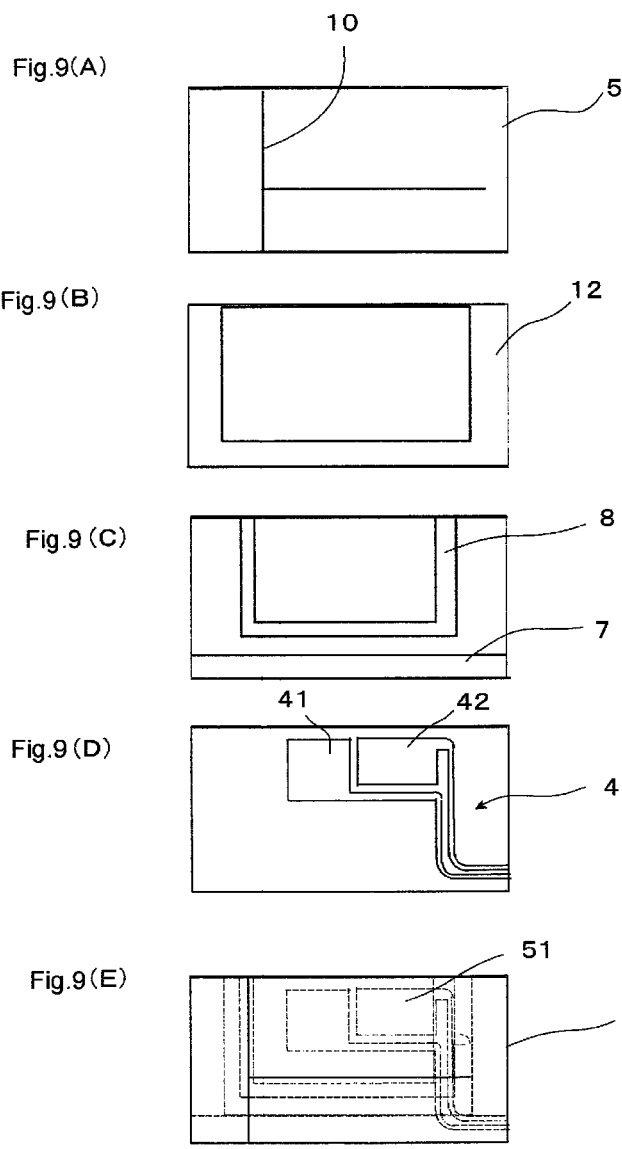

PRESSURE SENSOR, METHOD FOR MANUFACTURE THEREOF, AND PRESSURE DETECTION MODULE

BACKGROUND OF THE INVENTION

1. Field of the Invention

The present invention relates to a pressure sensor which can be formed integrally with a flexible circuit board, and which is suitable for the measurement of a pressure distribution used for a flexible curved surface including a spherical curved surface. The invention also relates to a method for manufacture thereof, and a pressure detection module.

2. Description of Related Art

General pressure distribution sensors commercially available in the market are each basically composed of a thin sheet of a quadrangular shape. Due to the sheet shape, such sensors can make measurements on a cylindrical curved surface, but are not suitable for measurements on a flexible curved surface including a spherical curved surface. This is because the sensors are associated with wire-saving technology (matrix wiring) in which signals are collected at pressure points including (N×M) points by the use of (N+M) wires, and so, the shape of a measurement region is limited to a quadrangular shape or the like, due to vertical and horizontal wiring.

In addition, these pressure distribution sensors, which are implemented by PET films and printed circuits, are becoming mainstream in use, but the wiring density is low because of low printing accuracy or migration of the wiring, and the wiring is not flexible and has no or little flexural bending resistance. Moreover, these sensors are not suitable for solder reflow, and hence, it is difficult for component parts to be mounted thereon, involving a problem that each sensor has to be connected to a signal processing device through a large-sized connector.

As a solution to these problems, there has been proposed a technology which achieves a tactile sensor capable of measuring a pressure distribution even on various curved surfaces, and which includes a tree-shaped substrate board provided with belt- or strip-shaped portions, and is based not on matrix wiring but on an IC type wire-saving scheme with component parts such as small-sized ICs capable of performing analog to digital conversion and communications being mounted on a sensor sheet (refer to a first patent document).

In a tree-shaped substrate board of this first patent document, in order to place pressure detection parts and wiring along the belt- or stripe-shaped portions, high-density wiring with a narrow space is required, and it is necessary to directly mount electronic parts on a substrate board for the purpose of IC type wire saving.

For that reason, use of a flexible circuit board used for general electronic equipment, instead of the above-mentioned general method using a PET film and a printed circuit, is suitable for the purpose of pressure detection.

In the first patent document, the construction of pressure sensors applied to the pressure detection parts is assumed to be arbitrary, but if existing pressure sensors are employed, there will be a problem that measurement errors occur, flexibility can not be made high, and reduction in size is difficult.

For example, a pressure detection mechanism used for a general pressure distribution sensor has a mainstream structure in which a pressure-sensitive resistance material or an elastic dielectric material is inserted between two sheets of films (for example, FlexiForce (trade name), Tekscan (trade name), etc., of NITTA Corporation).

However, in such a type of pressure distribution sensor, when it is bent, an internal pressure will be generated, which can not be distinguished from the case where an external pressure acts on the sensor, thus giving rise to a measurement error. This is because the curvatures of individual layers thus bent are different from each other, so in a bent portion, the individual layers try to come near to each other, thereby generating an internal pressure in the normal line direction of the sensor sheet. The value of the internal pressure becomes larger in accordance with the increasing curvatures.

In a bonding process to bond a spacer and a cover film to each other, an adhesive or bonding agent flows into a sensor portion, whereby the conductivity of electrodes is impaired and sensor characteristics are worsened. For this reason, the reduction in size is difficult. In particular, in cases where a plurality of sensors are to be mounted with high density, it is a difficult problem to make effective use of a limited adhesive or bonding area as well as to maintain a hollow structure of an electrode portion.

In a method in which a pressure-sensitive resistance material is coated, an elongation force may be generated along a film surface at the time of bending, thus resulting in an error. At the time of bending, in particular, in cases where the curvature of the bending changes in a dynamic manner, it is very difficult to make a distinction between such an internal pressure and an external pressure which is originally wanted to be measured, and this becomes a great cause of error in the pressure distribution measurement in a flexible curved surface.

In addition, in a sensor using matrix wiring, or in an electrostatic capacitive type sensor in which an elastic dielectric material is sandwiched between films at opposite sides, electrodes and wiring are required to be disposed on the films at opposite sides, so there is a problem that the sensor becomes thick and the flexibility thereof deteriorates. This means that an external force is required for the bending of the sensor itself, which also becomes an error with respect to an external force to be measured originally.

For the pressure detection parts, in addition to such a technique with a pressure-sensitive material, etc., being sandwiched, there is also another technique in which a pressure sensing element is mounted as a component part, but in this case, the pressure sensing element is mounted by means of solder reflow or a conductive adhesive or bonding agent, and hence, durability is low due to the peeling off of solder or the adhesive or bonding agent, resulting from their hardness, bending, etc. Moreover, there is a problem that adhesive bonding is high in implementation cost, etc. In particular, in the case of solder, there is also another problem that an extra or excessive region required in the surrounding of each solder plating portion, due to such as the size of each pad portion, the size of each opening portion of a cover lay, a mounting error, and so on, is large, thus making it difficult to achieve reduction in size and increase in packaging (wiring and mounting) density.

Further, as general pressure-sensitive resistance, there are mainly used ones in which an electrically conductive powder is dispersed in a binder such as rubber, etc., but it can not be said that these have high heat resistance. In order to coexist with solder reflow required for the bonding or adhesion process of the cover films as well as for IC type wire saving, a certain degree of heat resistance is also required, so it becomes necessary to pay careful attention to materials.

PRIOR ART REFERENCES

Patent Documents

First Patent Document: Japanese patent application laid-open No. 2007-78382

The present invention has been made in order to solve the problems of the conventional technologies as referred to above, and has for its object to provide a pressure sensor, a method for manufacture thereof, and a pressure detection module in which the sensor can be molded or formed with components of a flexible circuit board, and besides, is excellent in terms of low measurement error at the time of bending, high flexibility, miniaturization and high packaging density, heat resistance, etc.

In order to achieve the above-mentioned object, a pressure sensor according to the present invention is characterized by comprising:

a base film on which a conductor pattern having one or more electrodes is formed;

a cover film laminated on the base film so as to cover the electrodes of said conductor pattern; and a spacer disposed between said cover film and said base film so as to form a hollow portion having a predetermined gap between said electrode and said cover film;

wherein a portion corresponding to said hollow portion of said cover film is constructed such that it has a pressure sensing part which is able to deform in a direction to move toward and away from said electrode in accordance with pressure, and of which contact resistance changes in accordance with a contact pressure thereof with said electrode, so that the pressure sensing part detects the pressure by a change of the contact resistance.

With this construction, even if the sensor is bent, bending deformation thereof is absorbed by the hollow portion, so it is possible to reduce the generation of an internal pressure, thereby making it possible to decrease measurement errors.

In addition, the conductor pattern including the electrodes is formed only on the base film, and so it is thin, flexible and easy to bend. As a result, an external force required for bending itself is small, thus making it possible to further decrease measurement errors.

Moreover, the conductor pattern including the electrodes can be shaped or formed similarly to wiring layers of an ordinary flexible circuit board, thus making it possible to attain miniaturization and high wiring density.

Further, because the pressure sensor makes use of a contact resistance method, it serves to provide high heat resistance, and is also suitable for the reflow process required for IC type wire saving.

If a bank is arranged between said electrode and said spacer, at the time of adhering or bonding the cover film onto the spacer, the inflow of the molten adhesive agent to the hollow portion can be prevented, whereby the influence by the adhesive agent can be eliminated.

Said electrodes may be constructed as a pair of electrodes which are disposed side by side with said base film, or they can also be constructed such that one of the electrodes is disposed on said base film and is electrically connected to the pressure sensing part.

If the base film 2 has a belt-like or strip-shaped structure and said hollow portion is constructed to open at one side thereof to one side edge of the base film, flexibility of the base film 2 will become more higher, and measurement errors can be made low.

If plating of a metal conductor such as gold plating for prevention of oxidation, etc., is applied to a portion of said conductor pattern exposed to the hollow portion, deterioration due to the oxidation of the electrodes can be prevented.

In addition, plating requires a plating mask, but plating is not attached to that portion which is covered with the spacer such as a photosensitive cover, etc., so the conductor pattern formed of a copper foil, etc., can be completely protected by means of the photosensitive cover and the metal plating.

If said cover film is formed with a cut for reducing tensile force at the time of bending, the generation of internal pressure at the time of bending can be reduced to a further extent, so that measurement errors can be made still lower.

Moreover, if said pressure sensing part is a pressure sensing thin film deposited on said cover film, lamination of the pressure sensing part can be made within a manufacturing line for general flexible circuit boards, so that a special mounting process or step can be reduced, thus making it possible to achieve reduction in cost.

If said spacer or/and bank are composed of a photosensitive cover, the photosensitive cover can be processed into a fine shape by means of exposure and development using a mask, so a covered portion and an uncovered portion can be selected and prepared in an arbitrary manner, thus making it possible to form the hollow portion and the bank with a high degree of accuracy.

If protrusions are formed on the cover film, the cover film will become easy to be pushed into the hollow portion, thereby producing an effect to enhance initial sensitivity.

In addition, a method for manufacture of a pressure sensor according to the present invention is characterized by:

forming a conductor pattern provided with a pair of electrodes on a base film;

laminating a photosensitive cover on said base film, and removing at least a portion of said conductor pattern corresponding to said pair of electrodes thereby to cause said portion to be exposed, while covering a remaining portion of said conductor pattern with a remaining portion of said photosensitive cover;

applying metal plating treatment for prevention of oxidation to the exposed portion of said conductor pattern including said pair of electrodes; and forming, thereafter, a hollow portion in the removed portion of said photosensitive cover corresponding to said pair of electrodes, by laminating a cover film with a pressure sensing part formed thereon in advance in which contact resistance thereof changes according to a pressure of contact thereof with said electrodes, and by bonding said cover film to the remaining portion of said photosensitive cover by means of an adhesive agent.

The method is further characterized in that at the time of removing that portion of said photosensitive cover which corresponds to said pair of electrode, said photosensitive cover is used to shape, in front of said hollow portion, a bank which serves to prevent said adhesive agent from flowing into said hollow portion, and said cover film is non-bonded to said bank.

Moreover, another method for manufacture is characterized by:

forming a conductor pattern provided with one electrode on a base film;

laminating a photosensitive cover on said base film, and removing at least a portion of said conductor pattern corresponding to said electrode thereby to cause said portion to be exposed, while covering a remaining portion of said conductor pattern with a remaining portion of said photosensitive cover;

applying metal plating treatment for prevention of oxidation to the exposed portion of said conductor pattern including said electrode; and forming, thereafter, a hollow portion in the removed portion of said photosensitive cover corresponding to said electrode, by laminating a cover film with a pressure sensing part, in which contact resistance thereof changes according to a pressure of contact thereof with said electrode, and another electrode electrically connected to said pressure sensing part formed thereon in advance, and by bonding said cover film to the remaining portion of said photosensitive cover by means of an adhesive agent.

Further, in the above-mentioned method for manufacturing, it is preferable that at the time of removing that portion of said photosensitive cover which corresponds to said electrode on said base film, said photosensitive cover be used to shape, in front of said hollow portion, a bank which serves to prevent said adhesive agent from flowing into said hollow portion, and that said cover film be non-bonded to said bank.

In addition, a pressure detection module of the present invention is constructed to be provided with a flexible circuit board having one or more strip-shaped portions, and pressure sensors as mentioned above being disposed on the one or more strip-shaped portions which constitutes the flexible circuit board.

In this manner, by incorporating the pressure sensors into the flexible circuit board, the pressure sensors can also be made into intimate contact with a three-dimensional shape such as a spherical curved surface, so that a pressure distribution thereon can be detected in an accurate manner.

Moreover, if the plurality of strip-shaped portions are composed of a tree structure which branches in a hierarchical manner, and if a pressure sensor is arranged in an end portion of each of the strip-shaped portions, detection parts of the pressure sensors can be disposed with a much higher density.

Further, it can also be constructed such that the flexible circuit board is provided with one or more communication terminals, and one or more electronic circuit parts electrically connected to said pressure sensor and said communication terminals through wiring formed on said flexible circuit board, said electronic circuit parts each having a communication function to receive information received by each of said pressure sensors and to transmit the information to said communication terminals.

SUMMARY OF THE INVENTION

As explained above, according to the present invention, due to the formation of the hollow portion, high flexibility can be obtained, and the influence of bending can be made small, thereby making it possible to reduce measurement errors.

In addition, the conductor pattern can achieve high packaging or wiring density, similar to the wiring layers of a conventional flexible circuit board, thus making it possible to attain miniaturization.

Moreover, because of the use of contact resistance, the pressure sensor is also excellent in heat resistance and can be applied to solder reflow, etc.

Further, the pressure sensor is composed of materials which are used for the flexible circuit board, and hence, can be manufactured with ease by means of manufacturing facilities for conventional flexible circuit boards.

BRIEF DESCRIPTION OF THE DRAWINGS

FIG. 6 is a view showing a first pattern example, of a conductor pattern, a covering pattern of a photosensitive cover, and a cut pattern of the film cover, of a pressure sensor of the present invention.

FIG. 8 is a view showing a second pattern example, of the conductor pattern, the covering pattern of the photosensitive cover, and the cut pattern of the film cover, of a pressure sensor of the present invention.

FIG. 9 is a view showing a third pattern example, of the conductor pattern, the covering pattern of the photosensitive cover, and the cut pattern of the film cover, of a pressure sensor of the present invention.

DETAILED DESCRIPTION OF THE INVENTION

Conceptual Construction

First, reference will be made to a conceptual construction for carrying out the present invention.

A pressure sensor of the present invention has a structure in which a detection principle based on a contact resistance method is introduced, and implemented or embedded directly into the interior of a flexible circuit board.

Specifically, a structure with the pressure sensor embedded in the interior of the flexible circuit board is achieved by constructing the pressure sensor with the use of general-purpose component materials or elements of the flexible circuit board, such as a base film, a film cover, a photosensitive cover (PSC: Photo-Sensitive Cover), and so on.

This pressure sensor can construct a pressure detection part of a small-size by preventing an adhesive or bonding agent from flowing into electrodes by means of a bank, and hence, is not only suitable for increasing density, but also can suppress an internal pressure at the time of bending, by introducing a hollow structure. Moreover, the electrodes can be arranged collectively at a single side, thereby making it possible to improve the thinness and flexibility. In addition, the contact resistance method serves to provide heat resistance, and is also suitable for the reflow process required for IC type wire saving. As a result of this, the thinness and flexibility are increased to improve precision for measurement, and besides, mounting locations or portions such as soldering pads are made unnecessary, thereby improving reduction in size and increase in packaging (mounting or wiring) density as well as durability.

Further, it is possible to achieve the pressure sensor at low cost, without changing the existing manufacturing process for flexible circuit boards to a large extent.

Hereinafter, modes for carrying out the present invention will be described in detail by way of example with reference to the attached drawings. However, the dimensions, materials, shapes, relative arrangements and so on of component parts described in the following embodiment and modifications thereof are not intended to limit the scope of the present invention to these alone in particular as long as there are no specific statements.

Embodiment

1: Schematic Construction of Pressure Sensor

First, reference will be made to the schematic construction of a pressure sensor 1 according to an embodiment of the present invention, while referring to FIG. 1.

Figure 1A:
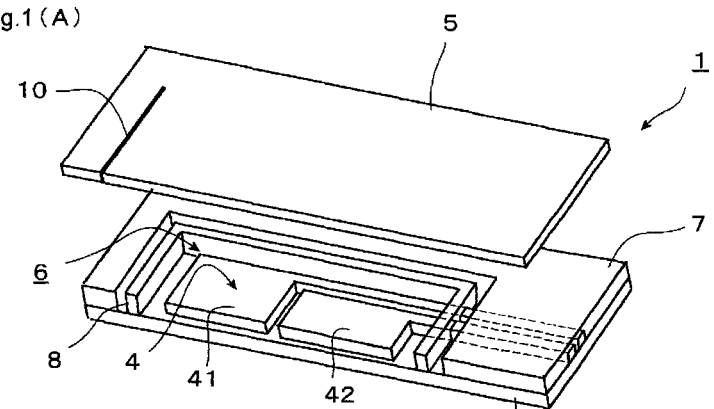
FIG. 1 shows the schematic construction of a pressure sensor according to a first embodiment of the present invention, wherein (A) is a schematic exploded perspective view in a state where a film cover is removed so that a hollow interior portion is exposed; (B) is a schematic exploded perspective view in a state where a film cover is closed; and (C) is a schematic cross sectional view showing the thickness of each part in an exaggerated manner.
Figure 1B:
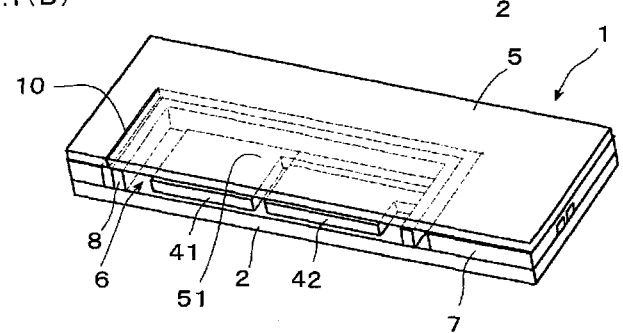
Figure 1C:
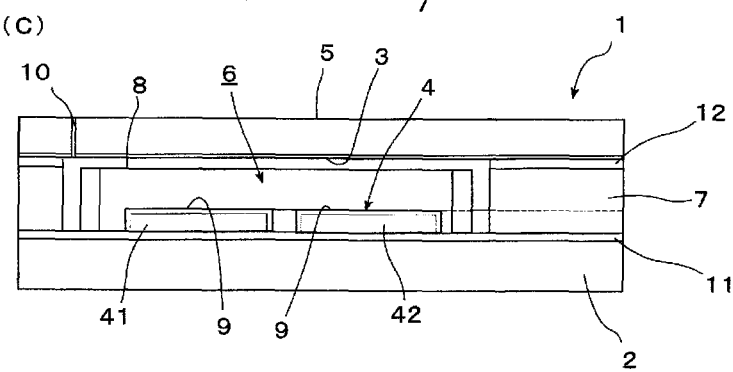
Figure 2A:
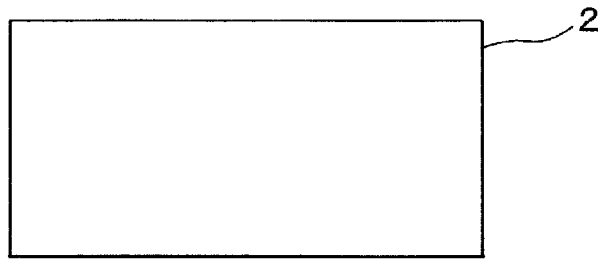
FIG. 2 (A) through (D) in FIG. 2 are plan views showing individual exploded layer constructions of the pressure sensor of FIG. 1, respectively.
Figure 2B:
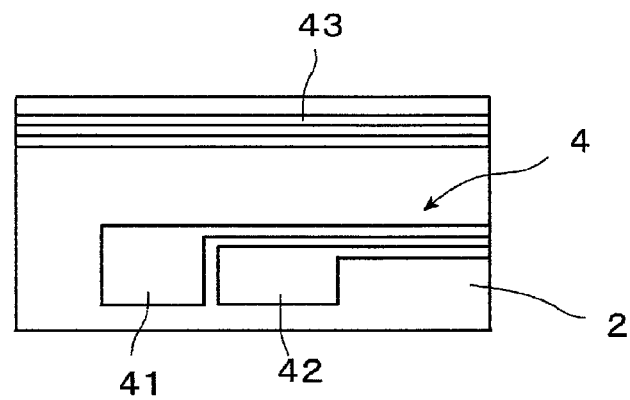
Figure 2C:
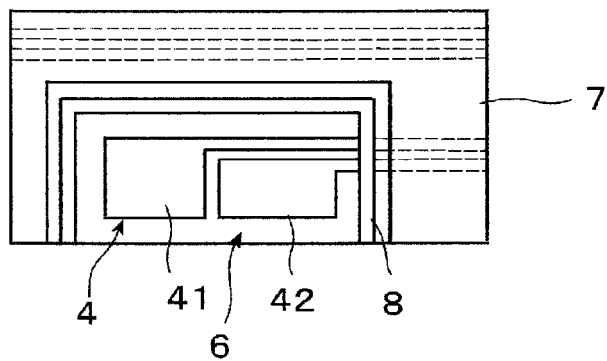
Figure 2D:
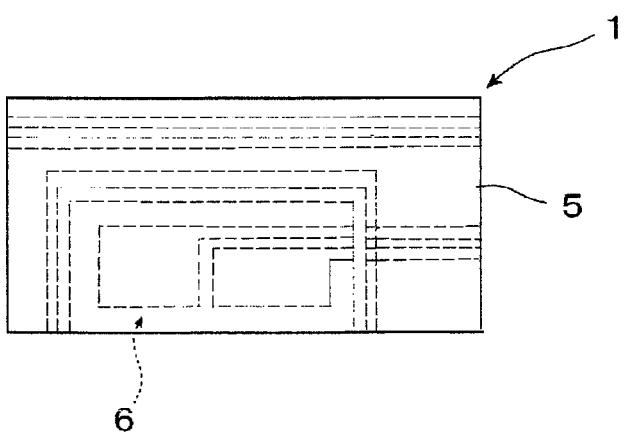
Figure 3A:
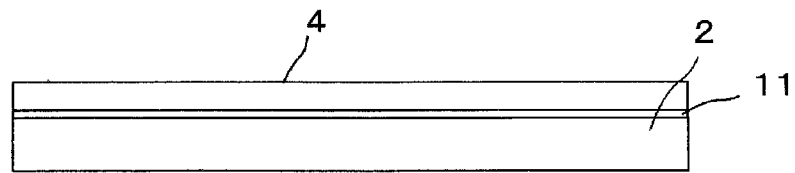
FIG. 3 (A) through (E) in FIG. 3 are cross sectional views showing the individual exploded layer constructions of the pressure sensor of FIG. 1, respectively.
Figure 3B:
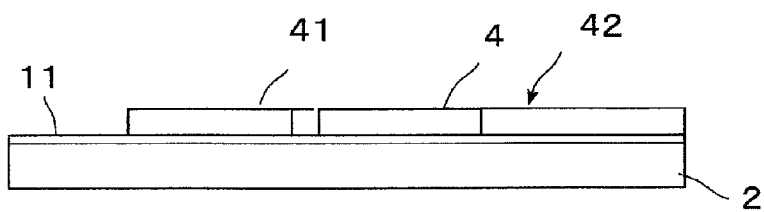
Figure 3C:
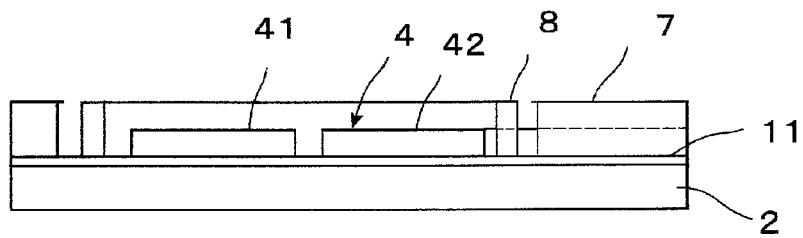
Figure 3D:
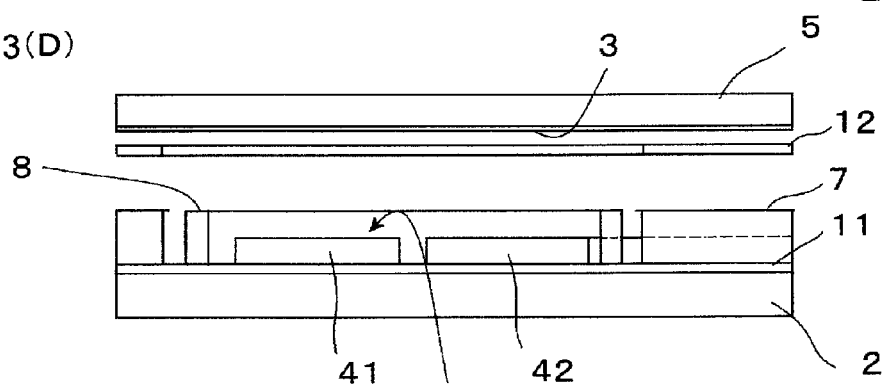
Figure 3E:
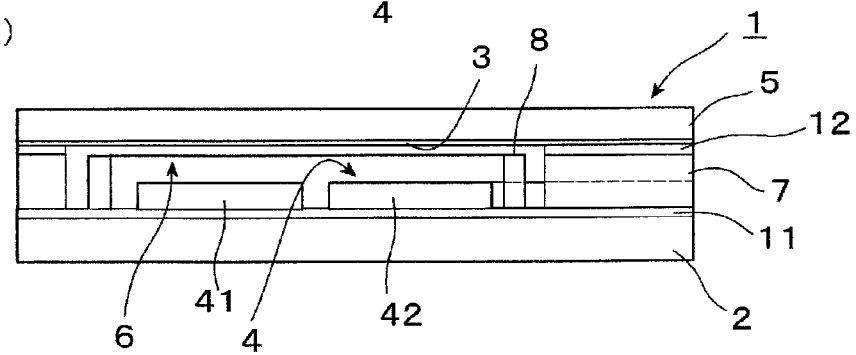
Figure 4A:
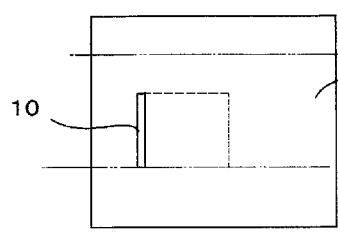
FIG. 4 (A) through (D) in FIG. 4 are explanatory views showing examples of a cut pattern, and (E) and (F) in FIG. 4 are explanatory views showing the relation of a cut position and a contact state of electrodes.
Figure 4B:
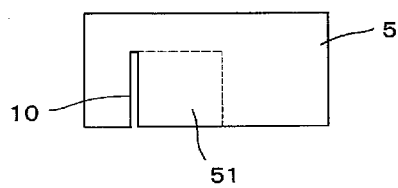
Figure 4C:
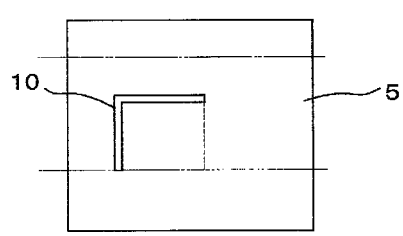
Figure 4D:
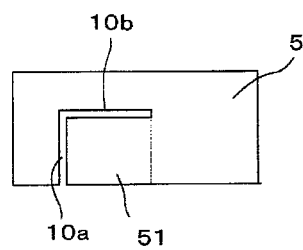
Figure 4E:
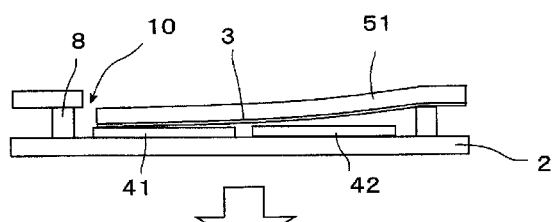
Figure 4F:
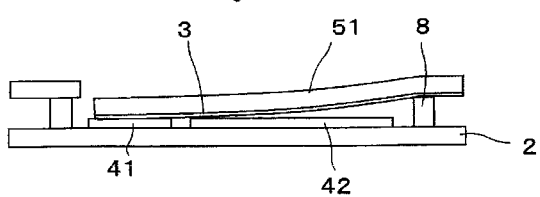

In FIG. 1, (A) is a schematic perspective view shown with a cover film removed; (B) is a schematic perspective view in a state where the cover film in (A) is laminated; and (C) is a schematic cross sectional view.

[Basic Construction]

As shown in FIG. 1, the pressure sensor 1 according to this embodiment is constructed such that a hollow portion 6 is formed in an arbitrary position between a base film 2, on which a conductor pattern 4 constructing a flexible circuit board is formed, and a cover film 5, and in the interior of the hollow portion 6, there are formed or arranged a pair of electrodes 41, 42. Then, by depositing a pressure sensing thin film 3 on a surface of the cover film 5 which faces the electrodes 41, 42, a pressure detection part is constructed which serves to detect a change of contact resistance at the time when pressure is applied thereto.

In order to construct the hollow portion 6, there are interposed between the base film 2 and the cover film 5 a bank 8, which is arranged so as to surround the hollow portion 6, and a spacer 7 which is further arranged so as to surround the bank 8. Here, note that in an illustrated example, a slit 10 is formed in the cover film 5. This slit 10 will be described later.

In this manner, in order to construct the pressure sensor 1, the electrodes 41, 42 are sandwiched by means of the two sheets of films, i.e., the base film 2 and the cover film 5 such as polyimide films, so that they are connected or adhered to the spacer 7.

The spacer 7 is composed of an adhesive or bonding agent by which the cover film 5 is bonded or adhered thereto, or is composed of a spacer material of a non-adhesive property laminated by the adhesive or bonding agent.

In cases where the cover film 5 is bonded or stuck to a mating material, a laminate coated in advance with the adhesive or bonding agent or bonded in advance with an adhesive sheet which has been subjected to shape processing is constructed, and is then laminated with the mating material by the application of temperature and pressure. According to this, it is possible to manufacture a multitude of pressure sensors in a large area and with a high degree of accuracy at once.

However, the adhesive agent becomes soft with heat at the time of lamination, and begins to flow out to a peripheral portion, so that it flows into a portion which is to be made into a hollow structure, thus giving rise to a problem that the hollow portion 6 is filled up or narrowed. Therefore, the bank 8 is modeled by making use of a photosensitive cover, printing ink, etc., so that the inflow of the adhesive agent is prevented by the bank 8.

In addition, polyimide, which is a general material for the flexible circuit board as the base film 2 or the cover film 5, transmits moisture and oxygen, and hence, it is possible to prevent from polyimide from being oxidized during a manufacturing process and in use by protecting the conductor pattern 4 including the electrodes 41, 42, etc., by means of either the spacer 7 or plating 9.

[Detailed Construction of Individual Parts]

Next, the individual layers mentioned herein will be explained in further detail.

[With Respect to the Base Film 2 and the Cover Film 5]

Polyimide films are used for the base film 2 and the cover film 5. Of course, they are not limited to the polyimide films, but for example, there can be used a single kind of film which is selected from, or a laminated film which is formed by laminating a plurality of resin films which are selected from, polyester, polyamide, polycarbonate, polyarylate, polyphenylene ether, poly phenylene sulphide, polyethersulfone, polyether imide, liquid crystal polymer, polyether ether ketone, cyclic polyolefin, polyamide imide, thermoplastic polyimide, polyethylene terephthalate, cycloolefin polymer.

Here, note that the base film 2 and the cover film 5 are each preferably a thin band-like construction of the same width, and the thickness thereof is preferably 5-100 µm, and in particular preferably 5-50 µm.

The materials used for the base film 2 and the cover film 5 may be the same material, or different materials may be selected for them, respectively.

[Conductor Pattern]

The electrodes 41, 42, which constitute the conductor pattern 4, are composed of flat or plate electrodes which are arranged in series away from each other at a predetermined space in a longitudinal direction along one side edge of the base film 2. In addition, as shown in (B) in FIG. 2, a plurality of wiring layers 43 extend at the other side edge of the base film 2.

The hollow portion 6 with the electrodes 41, 42 arranged therein is formed in a position offset to the one side edge of the base film 2 at the side of the electrodes 41, 42, and is opened at the one side edge. In this example, the hollow portion 6 takes a rectangular shape elongated in the longitudinal direction of the base film 2, wherein its one long side is its one side edge at the open side, and its short sides at the opposite ends in the longitudinal direction extend at right angles with respect to its one side edge at the open side, and its other long side extends in parallel with its one side edge at the open side.

The electrodes 41, 42 are composed of a well-known metal such as copper, silver, aluminum, etc., or a conductor such as carbon, etc., and are integrally formed as the conductor pattern 4. In this embodiment, the conductor pattern 4 is formed by means of a so-called subtractive process in which a rolled copper foil or an electrolytic copper foil laminated through the adhesive agent 11 on the surface of the base film 2 is subjected to etching processing. As other methods for forming the conductor pattern 4, there can be used the following methods. That is, the conductor pattern 4 can also be formed on the base film 2 by means of such methods as vapor deposition, sputtering, wet plating, etc., with the use of metal such as copper, or besides by printing of a conductive paste including silver, nano carbon, or the like.

The adhesive agent 11 is formed by using a well-known thermoplastic resin such as thermoplastic polyimide, or a well-known thermosetting resin such as cyanate ester based resin, polyphenylene ether based resin, phenol based resin, naphthalene resin, urea resin, amino resin, alkyd resin, silicon resin, furan resin, unsaturated polyester resin, epoxy resin, polyurethane resin, etc. Alternatively, the adhesive agent 11 can also be formed of any of the above-mentioned organic resins with an inorganic filler such as silica, alumina or the like dispersed therein.

[Introduction of the Contact Resistance Method]

In this embodiment, as a pressure sensing part, there is formed or deposited the pressure sensing thin film 3 on the cover film 5. This pressure sensing thin film 3 is composed of a material, regardless of organic or inorganic, which generates a change in contact resistance by being in contact with the electrodes.

In this example, the pressure sensor is constructed by combining the pressure sensing thin film 3 made of copper oxide, copper sulfide, or the like, which is formed on the cover film 5 composed of a polyimide film, and a conductor which is formed by applying gold plating to the surfaces of the electrodes 41, 42 using copper wiring of a flexible printed circuit (FPC).

That is, contact resistance existing between conductors generally increases and decreases due to a change in pressure, so such a phenomenon can be utilized for pressure detection. However, in the contact resistance of copper-to-copper pair, the resistance value thereof is decreased to a large extent by a slight amount of pressure, so wide dynamic range is not available, and it is difficult to use it for the purpose of pressure detection.

On the other hand, in the contact resistance by the combination of a semiconductor such as copper sulfide, copper oxide or the like and a conductor such as silver or gold, the contact resistance at the time of low pressure is several KΩ-several MΩ, and changes to several Ω-several KΩ as the pressure increases, and hence, there is a feature that the dynamic range can be made very large.

As a technique of forming the pressure sensing thin film 3 on a film, copper oxide can be formed by using a method of making copper oxide into a coating film on the polyimide film by sputtering, vapor deposition, etc., or a method of making a surface of the polyimide film into copper oxide by oxidizing a copper foil bonded onto the polyimide film, or a method of printing a copper ink or a cuprous oxide ink on the polyimide film, and then heating it in atmospheric air.

In this manner, by preparing the cover film 5 with the pressure sensing thin film 3 deposited thereon, lamination thereof can be made within a general FPC manufacturing line, so that a special mounting process or step can be reduced, thus making it possible to achieve reduction in cost.

[Spacer 7]

The spacer 7 is made of a photosensitive cover, a printing ink, or the like, and the spacer 7 and the cover film 5 are adhered to each other by means of the adhesive agent 12. The same material as the adhesive agent 11 can be used for the material of the adhesive agent 12. The spacer 7 can be made of the adhesive agent, so that it can also be formed as the same as the adhesive agent 12.

The photosensitive cover can form a protective film on the copper wiring with a high degree of accuracy, but is composed of a photo-curing resin which is not used for the purpose of adhering two sheets of polyimide films to each other.

In general, a film cover such as a polyimide film, etc., and a photosensitive cover are used as a cover lay separately according to their purpose. In cases where mechanical or chemical strength is required, the film cover is used, whereas in cases where the dimensional tolerance of the peripheral portions of the mounted component parts is required, and mechanical or chemical strength is not so required, the photosensitive cover is used. In cases where the film cover and the photosensitive cover are used in combination with each other, the film cover may be laminated, and the photosensitive cover may be partially used for a region which is not covered with the film cover.

In this embodiment, as a cover lay, there is used a two-layer structure of the cover film 5 of polyimide and the photosensitive cover which acts as the spacer 7, and first, an exposed region of the conductor pattern 4 including the electrodes 41, 42 is protected by the photosensitive cover, except for the electrode portion formed in the interior of the hollow structure.

Because the photosensitive cover can be processed into a fine shape by means of exposure and development using a mask, a covered portion and an uncovered portion can be selected and prepared in an arbitrary manner, thus making it possible to achieve a high degree of dimensional accuracy.

[Plating of Exposed Portion of the Conductor Pattern 4]

It is desirable that the electrodes 41, 42 arranged in opposition to the thin film 3 for pressure sensitivity be subjected to plating 9 such as gold plating, in order to prevent deterioration thereof. In general, plating treatment such as gold plating is carried out at a stage close to the last one after the cover lay, etc., has been applied, but in the case of this method, such plating treatment is carried out at a stage before pasting the cover film 5 is bonded or adhered. In this case, because wiring portions other than the electrodes 41, 42 are also exposed, gold plating will be carried out over an entire surface. When the entire surface is plated with gold, the cost will become high, and in nickel plating, flexibility thereof will be impaired and durability thereof will be deteriorated.

For that reason, it is desirable to protect the wiring portions other than the electrodes 41, 42 from the plating. In general, masking is carried out with the use of an adhesive seal, etc., but in order to construct a small-sized, high resolution pressure sensing element, masking with the adhesive seal can not provide good positional accuracy, and is difficult to use. Accordingly, it is desirable to introduce a method of covering with a thin photosensitive cover.

In cases where the photosensitive cover is used as the spacer 7, it can also be used as a plating mask.

[Structure of the Bank (Adhesive Agent Inflow Prevention)]

In this embodiment, the cover film 5 is bonded or stuck to the base film 2, with which the spacer 7 is covered, by means of the adhesive agent 12, whereby the hollow portion 6 is constructed in an electrode exposed region. The adhesive agent 12 is in a solid state at room temperature, but it is made to fluidize by being heated to a high temperature, and is adhered to the two sheets of films by being thermally set in a state placed in intimate contact with the two films.

In a contact resistance method, the pressure sensing thin film 3 and the electrodes 41, 42 need to be separated from each other, but the two sheets of films need to be adhered to each other except for the pressure sensing part. In this case, the two sheets of films should be thermally adhered after the adhesive agent is removed only from a pressure sensing part, but in a high temperature state, the adhesive agent will be fluidized to flow into the pressure sensing part.

Accordingly, by building an enclosure around the pressure sensing part by means of the bank 8 in advance, it is possible to prevent the liquefied adhesive agent from flowing into there. As in this embodiment, when the photosensitive cover is used, the structure of the bank 8 can be built with a high degree of finishing accuracy as well as a high degree of positional accuracy.

In addition, such a structure of the bank 8 can also play the role of preventing the pressure sensing part from coming into contact with the electrodes 41, 42 at the time of no load.

In this example, the bank is formed in the shape of C character so as to surround three sides of the hollow portion of rectangular shape.

The methods for use and the structure for such as the protection of the spacer 7 and the conductor pattern by the photosensitive cover, as well as the prevention of the inflow of the adhesive agent by the bank 8, etc., in the pressure sensor 1 as constructed in this manner are original techniques of the present invention, and can be achieved without impairing mass productivity, thus making it possible to manufacture the pressure sensor with a non-conventionally large area and high density at low cost.

[Protrusions in the Sensor Portion]

Although this sensor has a feature of a thin shape like a film, an initial load is required due to the hollow structure. In cases where higher sensitivity is required, if small protrusions are formed on the cover film 5 above the hollow portion 6, the cover film 5 will become easy to be pushed into the hollow portion, thereby producing an effect to enhance initial sensitivity.

Protrusions with a height of several μm-several tens μm may be formed in an upper portion of a back surface of the pressure sensing thin film 3 of the cover film 5 of the pressure detection part, so that sensitivity can also be increased so as to detect even a slight or very small pressure by the protrusions being pushed from the outside.

It can be considered that the protrusions are formed by a variety of methods, such as by using printing, resin, adhesive agent, etched copper foil, punching of a film, and so on.

[Paired Electrode Structure]

In the above explanation, there has been shown an example in which the electrodes 41, 42 are formed only on the base film 2, but one electrode may be formed on the base film 2, with another electrode being formed on the cover film 5. In addition, the pressure sensing thin film 3 can also be formed on each of the electrodes. In this case, although flexibility becomes worse, the area of each of the electrodes can be made large, thus making it possible to enhance sensitivity.

[Enclosure]

Here, note that the hollow portion is not limited to a one-sided open structure in which a side face is opened, but may also take a closed construction in which the hollow portion is sealed or closed.

Similarly, the bank 8 is not limited to the shape of C character, but may be constructed in such a shape as to fully enclose or surround the entire electrodes.

[Method for Manufacture]

Next, a method for manufacture of the above-mentioned pressure switch will be explained below with reference to FIG. 2 and FIG. 3.

The cover film 5 is prepared in advance on which the pressure sensing thin film 3 has been formed in advance, wherein the contact resistance of the thin film 3 changes according to the contact pressure thereof with the electrodes.

First, on the base film 2, the conductor pattern 4 including the one pair of electrodes 41, 42 and the various kinds of wiring layers 43 is formed by means of the subtractive process, etc., as mentioned above (refer to (A) and (B) in FIG. 2, and (A) and (B) in FIG. 3).

Then, the spacer 7 and the photosensitive cover, which will become the bank 8, are laminated on the base film 2 on which the conductor pattern 4 has been formed. Then, in order to expose at least those portions of the photosensitive cover which correspond to the pair of the electrodes 41, 42 of the conductor pattern 4, the photosensitive cover is exposed and developed, and the remaining portion (other than the electrodes) of the conductor pattern 4 is covered with the remaining (i.e., non-exposed and non-developed) portion of the photosensitive cover (refer to (C) in FIG. 2 and (C) in FIG. 3).

Subsequently, metal plating treatment for prevention of oxidation is carried out on the exposed portions of the conductor pattern 4 including the one pair of electrodes 41, 42 (not shown).

Thereafter, the cover film 5 prepared in advance is laminated, and the base film 2 is bonded to the cover film 5 through the spacer 7 by means of the adhesive agent 12, so that the hollow portion 6 is formed in the exposed portions of the one pair of electrodes 41, 42 in which the spacer 7 is not placed (refer to (D), (E) in FIG. 2, and (D), (E) in FIG. 3).

In addition, when the spacer 7 is formed from the photosensitive cover, the bank 8 is shaped so as to surround the hollow portion 6, so that the inflow of the adhesive agent 12 to the hollow portion 6 is prevented. The bank 8 should not be bonded or adhered to the cover film 5.

[Operation of the Pressure Sensor]

Next, reference will be made to the operation of the pressure sensor according to this embodiment.

The one pair of electrodes 41, 42 are connected to an unillustrated current source. In a state where pressure does not act, the pressure-sensitive portion 51 of the cover film 5, which corresponds to the hollow portion 6, and the electrode 42 are away from each other, so that an electric current does not flow through between the electrodes 41, 42.

When a predetermined pressure acts, the pressure-sensitive portion 51 corresponding to the hollow portion 6 will flexurally deformed, and the pressure sensing thin film 3 will be placed into contact with the electrodes 41, 42, whereby the contact resistance therebetween changes in accordance with the contact pressure, and the electric current flowing between the electrodes changes.

In cases where a pressure-sensitive resistance material is used for the pressure sensing thin film 3, the resistance value changes to a large extent due to a change of the electric resistance resulting from the pressure in the pressure sensing thin film 3 itself, in addition to the contact resistance, so that this change of the electric resistance is taken out as an electrical signal, thereby detecting the pressure.

In addition, even if the pressure-sensitive portion 51 is simply bent to deform, such a deformation is absorbed to some extent by an initial gap in the hollow portion 6, so that measurement errors due to bending can be reduced.

The base film 2 has a belt-like or strip-shaped structure, and the above-mentioned hollow portion 6 is opened at one side thereof to the one side edge of the base film 2, and hence, the pressure-sensitive portion 51 is easy to deform in accordance with a change in pressure. In addition, air in the hollow portion 6, flowing from and to the outside, does not obstruct the deformation of the pressure-sensitive portion 51.

[Reduction of the Internal Pressure Due to the Cut]

In addition, a cut 10 is made in the cover film 5, so that a tensile force acting on the cover film 5 at the time of bending can be reduced. As a result, the internal pressure due to bending will be decreased.

FIG. 4 schematically shows the cut shapes in cases where an I-character cut is made in the cover film 5 of the pressure sensor, and an L-character cut is made therein.

Figure 5:
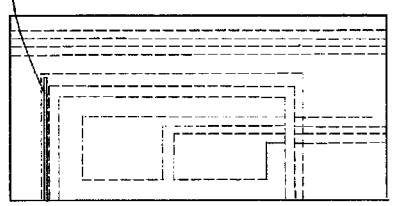
FIG. 5 is an explanatory view showing an example in which cutting is made into the pressure sensor.
Figure 5:
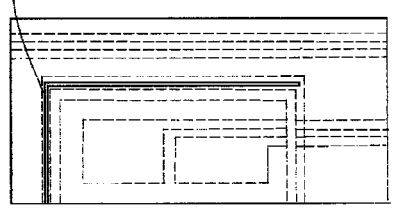
Figure 5C:
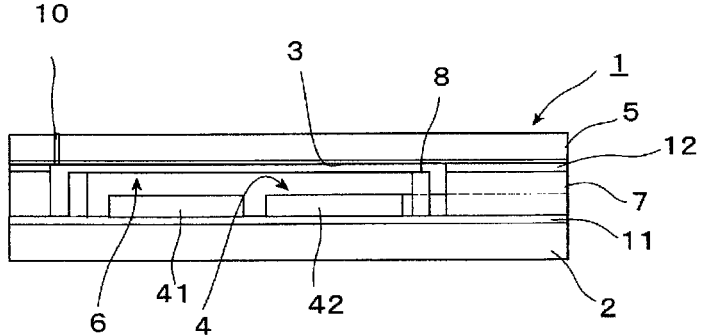

(A) and (B) in FIG. 4 show an example of the I-character cut. The cut 10 of FIG. 1 is an example of this I character cut, and (A) in FIG. 5 is a plan view of the pressure sensor in FIG. 1. The cut 10 cuts the pressure-sensitive portion 51 of the rectangular shape corresponding to the hollow portion linearly at right angles from a side edge thereof at its open side. In this case, the tensile force can not be canceled out completely. Instead, it can be said that the production itself is simple. Although the cut 10 does not cut through to an opposite side edge in FIG. 4, such (cutting through) is also possible.

(C) and (D) in FIG. 4 show an example of the L-character cut. (B) in FIG. 5 shows a structure example in which the cut in FIG. 1 is formed as the L-character cut. The cut 10 is in the shape of an L character, wherein the pressure-sensitive portion 51 of the rectangular shape corresponding to the hollow portion is composed of a lateral slit 10a extending at right angles from a side edge thereof at its open side, and another slit 10b.

When the cut 10 is made in the shape of L in this manner, the pressure-sensitive portion 51 corresponding to the hollow portion will be in a cantilever state, thus making it possible to bring the internal pressure at the time of bending to substantially zero. In this case, the internal pressure can be completely canceled out, but on the other hand, cutting work is difficult, and so, both (the I-shaped cut and the L-shaped cut) are used properly or selectively in accordance with the situation.

[Relation Between the Cut and the Electrode Shape]

In (E) and (F) in FIG. 4, there is shown the positional relationship between the cut 10 and the electrodes 41, 42.

As for the shape of the electrodes, in general, there is often used a comb-type shape in which a pair of combs are placed in mating engagement with each other, but in the comb-type shape, as the shape becomes smaller, the effective surface area of contact between the comb-shaped electrodes become smaller. As a result, in the case of a small-sized pressure sensor, two simple parallel electrodes 41, 42 are suitable.

In addition, as the size of the electrodes becomes smaller, the thickness of the adhesive agent, etc., may have a significant influence with respect to the size of the electrodes 41, 42. In other words, in cases where the pressure-sensitive portion 51 corresponding to the hollow portion 6 is pushed from above, contact thereof with the electrodes will begin from the neighborhood of the cut 10, and a contact surface thereof will change so as to spread to a root side in a gradual manner.

For that reason, if a division (or separation) position of the electrodes is simply set to be the center thereof, there is a fear that localized or partial contact may occur, as shown in (E) in FIG. 4. Accordingly, it is preferable to set the two electrodes 41, 42 in such a manner as to bring them near to the cut 10, as shown in (F) in FIG. 4.

When the pressure-sensitive portion 51 in a pressure detection region is divided into two parts in parallel to a longitudinal direction thereof, it will become almost impossible for the electrode at the root side of the pressure-sensitive portion 51 to be brought into contact therewith, for the same reason as mentioned above, and hence, it is necessary to divide the pressure-sensitive portion into two parts at right angles to the longitudinal direction.

FIGS. 6 and 8 through 10 are views showing a variety of kinds of modifications, of the conductor pattern, the covering pattern of the photosensitive cover, and the cut pattern of the film cover, of the pressure sensor of the present invention.

The basic construction of the modifications is the same as the construction of the pressure sensor explained in the above-mentioned embodiment, and hence, the same component parts as those of the above-mentioned embodiment are denoted by the same reference numerals and characters, and the explanation thereof is omitted.

First Modification

FIG. 6 shows a first modification, wherein (A) shows a pattern of a cut 10; (B) shows a pattern of an adhesive agent 12; (C) shows a covering pattern of a spacer 7 and a bank 8; (D) shows a conductor pattern 4; and (E) shows an overlapped state of these patterns.

This first modification is constructed as follows. That is, the cut 10 in a cover film 5 is in the shape of a T character, instead of the L character (refer to (A) in FIG. 6), and when the cover film 5 is bonded to a base film 2 with which the spacer 7 is covered, by means of the adhesive agent 12, a pressure-sensitive portion 51 corresponding to a hollow portion 6 becomes a cantilever structure in which a free end thereof is in abutment on the bank 8 (refer to (E)).

The free end of the pressure-sensitive portion 51, which receives pressure and is deformed thereby, rides on the bank 8, thus providing an effect of preventing unexpected contact between electrodes 41, 42 and the cover film 5.

Since the distances between a side portion of the bank 8 and the electrodes 41, 42 are short, a region of the wiring layer 43 required to be covered by a photosensitive cover can be taken wide, so that the number of wiring lines can be increased with respect to the base film 2 of the same width.

The pressure sensor used for this measurement was made as follows. A copper oxide film was formed, as a pressure sensing thin film 3, on the cover film 5 composed of a polyimide sheet by means of sputtering, and an adhesive sheet 12, which had been subjected to shape working in advance, was bonded to the copper oxide film thus formed, thereby preparing a base material. The conductor pattern 4 was formed by applying etching processing to a copper foil laminated on the base film 2, and the photosensitive cover was laminated on the conductor pattern 4 thus formed, which is then exposed and developed. Thereafter, nickel and gold were plated on the surfaces of the electrodes 41, 42, and the cover film 5 was laminated thereon. In this manner, the pressure sensor was made as an experiment.

Figure 7:
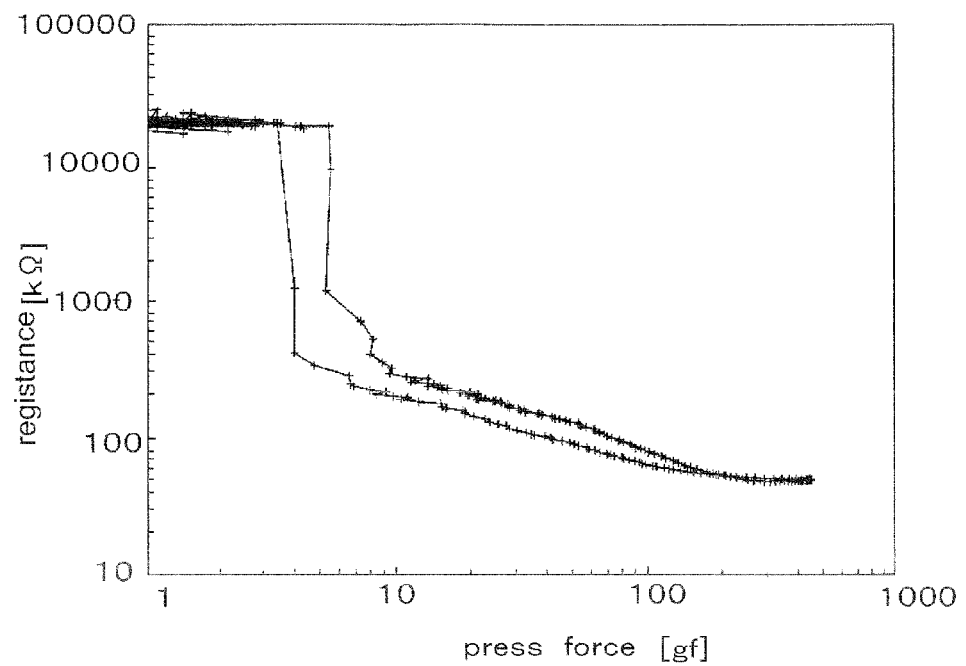
FIG. 7 is a graph showing an example of pressure and a change in the value of resistance.
Figure 10A:
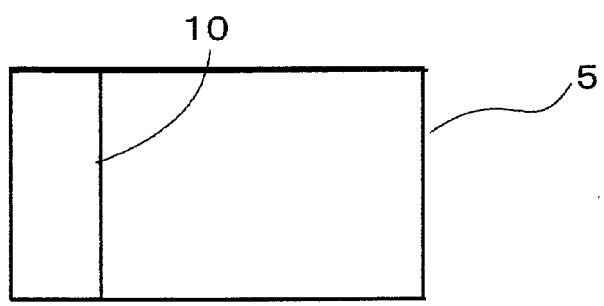
FIG. 10 is a view showing a fourth pattern example, of the conductor pattern, the covering pattern of the photosensitive cover, and the cut pattern of the film cover, of a pressure sensor of the present invention.
Figure 10B:
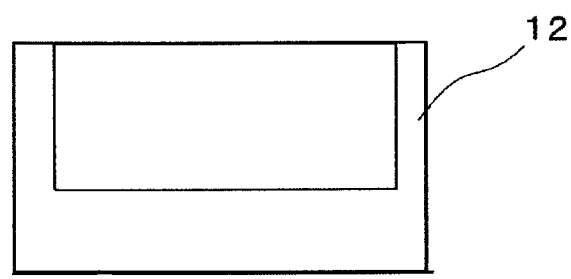
Figure 10C:
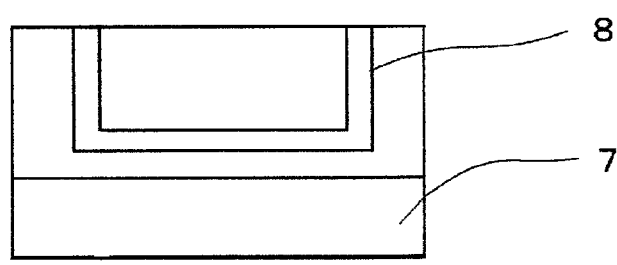
Figure 10D:
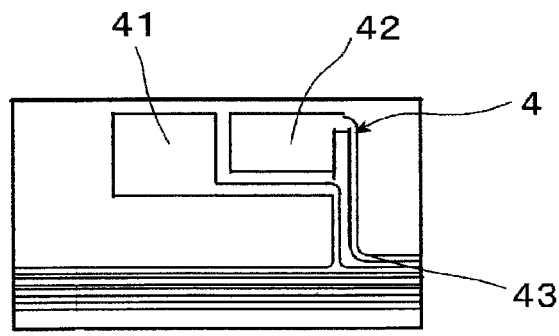
Figure 10E:
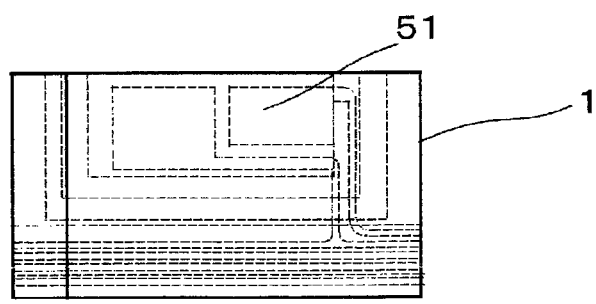

FIG. 7 shows a measurement example of the pressure detection characteristics of this pressure sensor, wherein an axis of abscissa represents a force (log scale), and an axis of ordinate represents a resistance value. It was verified that a resistance change occurred in accordance with pressure, and that the measurements of the pressure and a pressure distribution were able to be carried out with good reproducibility.

Second Modification

FIG. 8 shows a second modification, wherein (A) shows a pattern of a cut 10; (B) shows a pattern of an adhesive agent 12; (C) shows a covering pattern of a spacer 7 and a bank 8; (D) shows a conductor pattern 4; and (E) shows an overlapped state of these patterns.

This second modification is constructed such that the cut 10 in a cover film 5 is a through cut in the shape of an I character (refer to (A) in FIG. 8), and a pressure-sensitive portion 51 of a hollow structure is adhered at two vertical and horizontal sides thereof to the spacer 7 by means of the adhesive agent 12. With such a construction, a free end of the pressure-sensitive portion 51 rides on the bank 8, thereby making it possible to prevent unexpected contact between electrodes 41, 42 and the cover film 5.

Third Modification

FIG. 9 shows a third modification, wherein (A) shows a pattern of a cut 10; (B) shows a pattern of an adhesive agent 12; (C) shows a covering pattern of a spacer 7 and a bank 8; (D) shows a conductor pattern 4; and (E) shows an overlapped state of these patterns.

In this third modification, the cut 10 in a cover film 5 is in the shape of a T character (refer to (A) in FIG. 9), and when the cover film 5 is bonded to a base film 2 through the spacer 7 by means of the adhesive agent 12, a pressure-sensitive portion 51, which is of a hollow structure and adapted to receive pressure, has a cantilever structure, but a free end of a lateral or horizontal side does not ride on the bank 8.

The pressure-sensitive portion 51, being of the hollow structure, becomes easy to contact electrodes 41, 42, thus making it possible to achieve high sensitivity. In addition, the bank 8 surrounding or enclosing the electrodes 41, 42 become large, thereby reducing a wiring area and a bonding area.

Fourth Modification

FIG. 10 shows a fourth modification, wherein (A) shows a pattern of a cut 10; (B) shows a pattern of an adhesive agent 12; (C) shows a covering pattern of a spacer 7 and a bank 8; (D) shows a conductor pattern 4; and (E) shows an overlapped state of these patterns.

This fourth modification is constructed as follows. That is, the cut 10 in a cover film 5 is in the shape of an I character (refer to (A) in FIG. 10), and when the cover film 5 is bonded through the spacer 7 to the base film 2 by means of the adhesive agent 12, a pressure-sensitive portion 51 of a hollow structure is adhered at two vertical and horizontal sides thereof to the spacer 7, but a free end of the pressure-sensitive portion 51 does not ride on the bank 8 (refer to (E) in FIG. 10).

According to such a construction, electrodes 41, 42 and the cover film 5 become easy to contact with each other, thus making it possible to achieve high sensitivity. Due to the I-character cut, the structure can be simplified, thus making it possible for a wiring area and a bonding area to be taken widely.

Figure 11A:
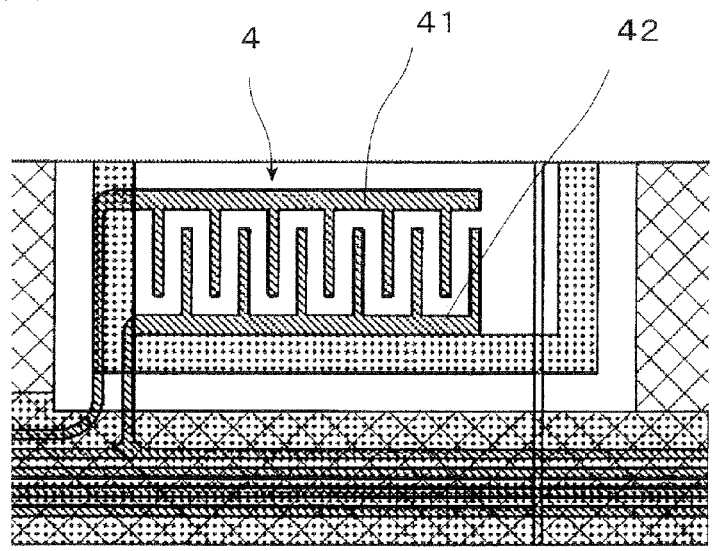
FIG. 11 (A) in FIG. 11 is a view showing another pattern of other electrodes of the pressure sensor of the present invention, and (B) in FIG. 11 is a view showing a pattern example in the case of the provision of a reinforcing plate in a pressure sensor of the present invention.
Figure 11B:
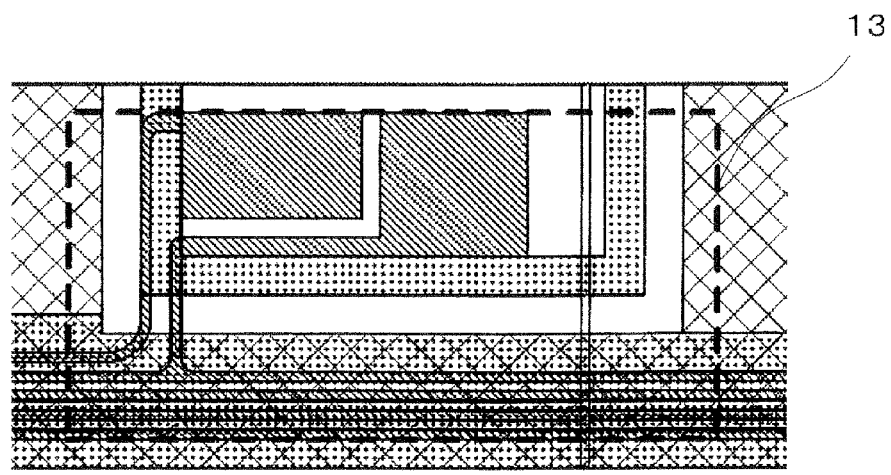

In addition in the structure of each of the various kinds of above-mentioned modifications, with respect to the shape of the electrodes 41, 42, it is possible to form them in the shape of a comb, as shown in (A) in FIG. 11.

Further, as shown in (B) in FIG. 11, a copper pattern can be left at the back side of the pressure sensor 1, so that it can also be made to act as a reinforcing plate 13. If reinforced in this manner, the sensing performance of the pressure sensor 1 can be improved.

[Modularization by Electronic Packaging]

Figure 12:
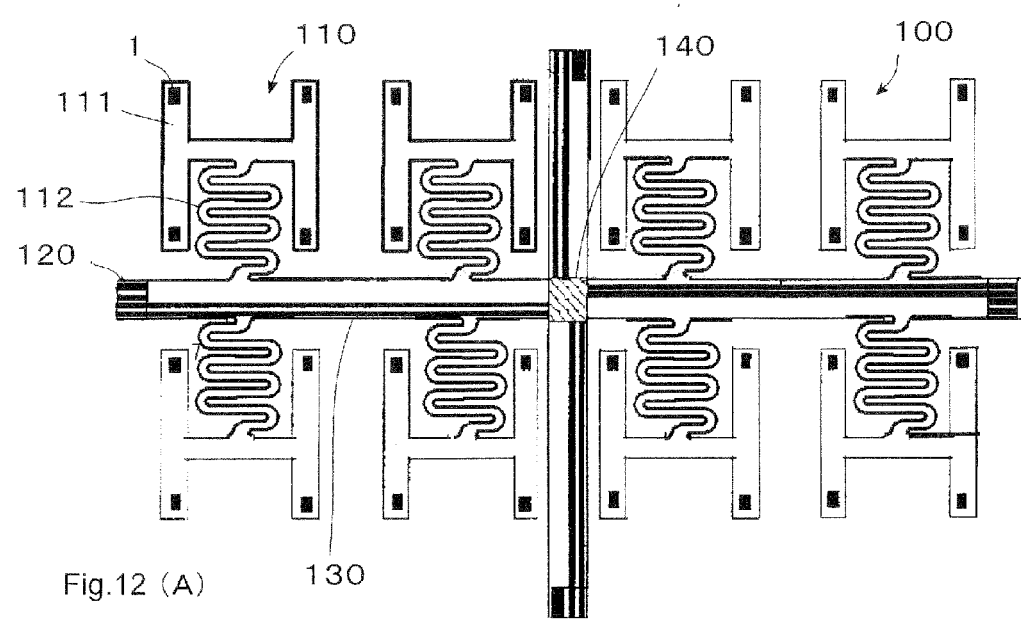
FIG. 12 (A) in FIG. 12 is a view showing a pressure detection module to which a pressure sensor of the present invention is applied; (B) in FIG. 12 is a view showing an example of the application of the pressure detection module of the present invention; and (C) in FIG. 12 is a view showing another pressure detection module.
Figure 12:
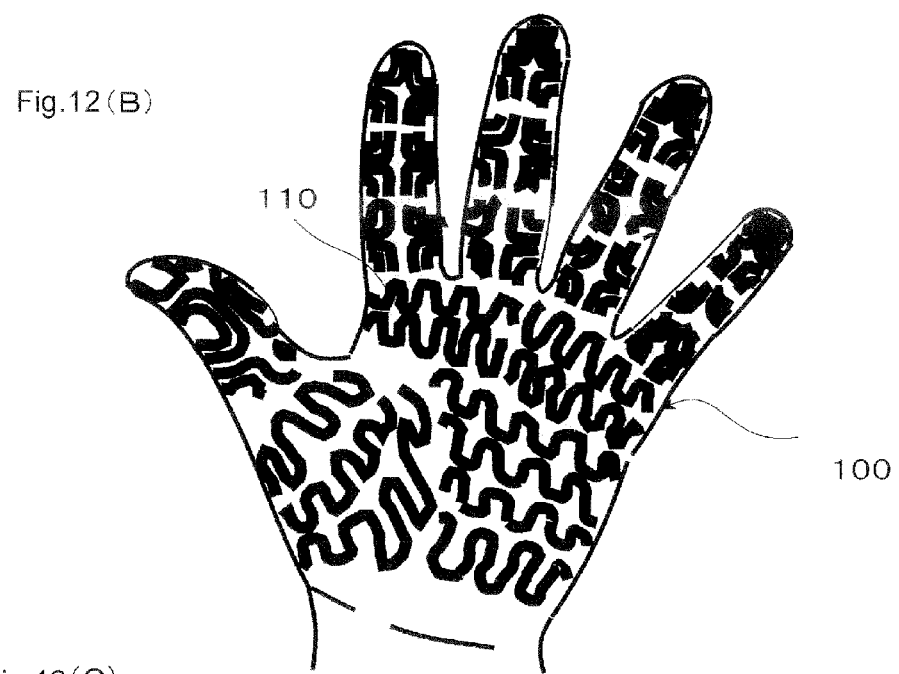
Figure 12:
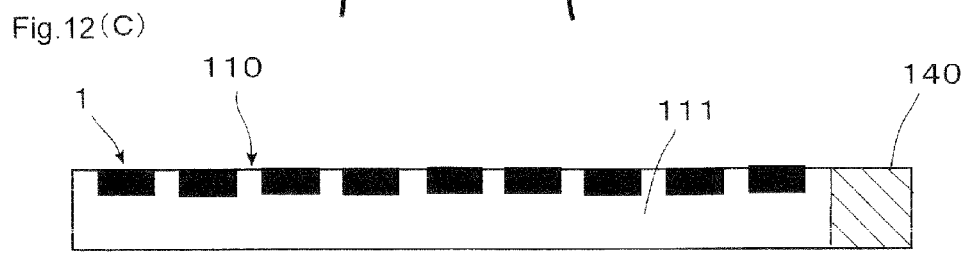

(A) through (C) in FIG. 12 shows pressure detection modules using pressure sensors of the present invention.

A pressure detection module shown in (C) in FIG. 12 is constructed to be provided with a flexible circuit board 110 having a single or monolithic belt- or strip-shaped portion 111, and a plurality of pressure sensors 1 of the present invention as mentioned above being disposed on the belt- or strip-shaped portion which constitutes the flexible circuit board. The pressure sensors 1 are arranged in row in side edges of the strip-shaped portion 111.

The pressure detection module 100 is constructed to be further provided with one or more communication terminals formed on the flexible circuit board 110, and one or more electronic circuit parts 140 formed on the flexible circuit board 110 and each having a communication function to transmit information on the pressure sensors 1 to the communication terminals.

Although the shape shown in (C) in FIG. 12 is a single belt or strip, this may be a tree shape which is composed of a plurality of belts or strips, or the shape of a belt or strip may be a wave shape.

In this manner, the flexible wiring board has heat resistance, the mounting of component parts thereon is possible, and electronic component parts or ICs can be mounted in necessary portions of the wiring board. According to these, it becomes possible to carry out signal processing and communication control in the periphery or surrounding of each pressure sensor. Because there is no need for connection to external substrate boards, wire saving and weight reduction or saving can be made, and it can also be considered that if necessary, a temperature sensor and/or other sensors are mounted for use as a composite sensor module.

A pressure detection module 100 shown in (A) in FIG. 12 is constructed to be provided with a flexible circuit board 110 having a plurality of strip-shaped portions 111, and pressure sensors 1 of the present invention as mentioned above being disposed on the strip-shaped portions which constitute the flexible circuit board. The plurality of the strip-shaped portions 111 are composed of a tree structure which branches in a hierarchical manner, and the pressure sensors 1 are arranged in end portions of each of the strip-shaped portions 111. In particular, the strip-shaped portions of the tree structure are constructed in such a manner that they are connected with a trunk strip-shaped portion through zigzag-shaped portions 112, respectively, so as to make wiring portions between the pressure sensors 1 easy to deform more following a flexible surface.

The pressure detection module 100 is constructed to be further provided with one or more communication terminals 120 formed on the flexible circuit board 110, and one or more electronic circuit parts 140 formed on the flexible circuit board 110 and electrically connected to the communication terminals 120 through wiring 130 extending from the flexible circuit board 100, electronic circuit parts each having a communication function to transmit information on the plurality of pressure sensors 1 to the communication terminals.

The form of the pressure detection module can be changed into various constructions in accordance with an application site or part. For example, in (B) in FIG. 12, a pressure sensor(s) is (are) integrally formed in an arbitrary location(s) of a belt- or strip-shaped flexible circuit board 110.

As a structure and a technique for manufacturing pressure sensors and a pressure detection module with a large area and high density at low cost, it is effective to adopt not only a method of manufacturing all pressure sensing parts by laminating them at once in roll to roll form, but also a method of bonding them to each other in cut sheet form, or laminating them partially, or mounting the sensing parts separately and individually.

With the above, it is possible to construct a composite sensor system by combinations of not only one kind of sensors but also other kinds of sensors, although it is necessary to manufacture the sensing parts in advance in order to mount the sensing parts individually.

Moreover, it is possible to mount sensors only at arbitrary locations, so a sensor system can be built in a very efficient manner by fabricating a standard sensor matrix structure in advance, and mounting sensing parts only at necessary locations.

However, electrode structures are required for the sensor matrix structure and the sensing parts for the purpose of mounting thereof, thus resulting in some increase in cost as well as an increase in thickness. Accordingly, it is recommended to take a package laminate technique, a partial laminate technique, or a partial packaging technique according to a purpose.

Here, note that in the description of the above-mentioned embodiment, explanation has been given to the case in which a pressure sensor is of a strip-shaped structure and has a hollow portion with its one side opened, but the pressure sensor may not be limited to the strip-shaped structure, and the hollow portion may not be opened. In other words, the construction should only be as follows. That is, the hollow portion is formed at arbitrary locations of the base film and the cover film which constitute the flexible circuit board, and the electrodes are formed, with the bank surrounding the electrodes, wherein the pressure sensing thin film corresponding to the hollow portion is placed into contact with a pressure, so that the pressure can be detected by means of the contact resistance method.

Figure 13A:
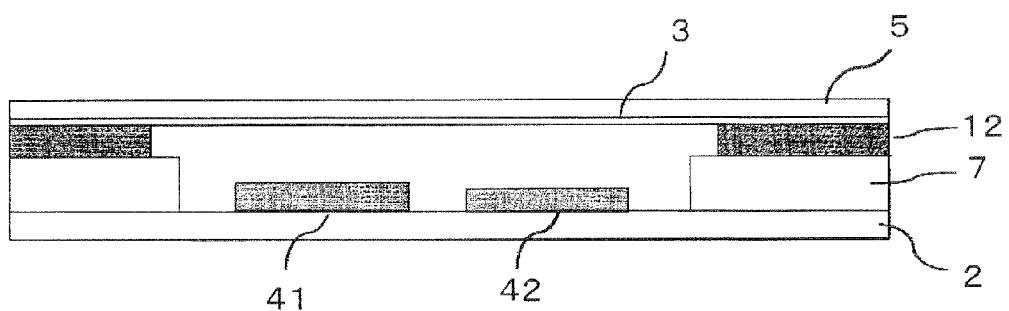
FIG. 13 shows the schematic construction of another pressure sensor according to the present invention, wherein (A) in FIG. 13 is a schematic cross sectional view showing an example in which an end face of an adhesive sheet is retreated from a photosensitive cover which acts as a spacer, and (B) in FIG. 13 is a schematic cross sectional view showing an example in which a photosensitive cover is used only as a bank.
Figure 13B:
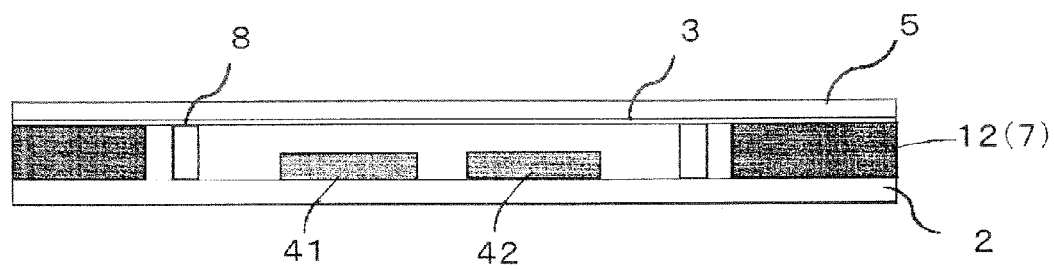

For example, as shown in (A) in FIG. 13, the bank 8 is not provided, but an end face of the adhesive sheet 12 is retreated from an end face of the spacer 7 which is composed of the photosensitive cover, thereby making it possible to also ensure a region by which the fluidized adhesive agent is held not to flow into the hollow portion at the time of thermocompression bonding. As shown in (B) in FIG. 13, the photosensitive cover is used only as the bank 8, and in those portions other than that, the cover film 5 and the base film 2 are bonded to each other by means of the thick adhesive sheet 12, so that the adhesive sheet 12 may be used as the spacer 7. Even if the pressure sensor is made small in size, in order to escape the influence of inflow of the adhesive agent on the performance of the pressure sensor, it is important to construct the pressure sensor in such a manner that the adhesive agent does not flow into the hollow portion.

FIELD OF INDUSTRIAL APPLICATION

A pressure sensor and a pressure detection module of the present invention are suitable for use requiring a low rate of measurement error and a high resolution, mainly in the measurement of pressure distribution on curved surfaces including various spherically curved surfaces, in particular a flexible curved surface which has a small curvature and in which a dynamic curvature change can occur (hereinafter expressed as a flexible curved surface), etc.

For example, a body surface of a human or robot, or a surface of an object being in contact therewith becomes a typical object to be measured. The main fields of application can be widely found in tactile sensors for fingers or soles (input devices of information machines and equipment, development evaluation of products to be taken by hand), tactile sensors of robot hands artificial limbs, pressure pattern measurement of chairs or beds (medical welfare, product development evaluation), pressure distribution measurement of fuselages or hands and feet (medical care, for motion measurement, clothing and accessories development), etc.

EXPLANATION OF REFERENCE NUMERALS AND CHARACTERS

1 . . . pressure sensor,
2 . . . base film,
3 . . . pressure sensing thin film,
4 . . . conductor pattern,
5 . . . cover film,
41, 42 . . . electrodes,
6 hollow portion,
7 . . . photosensitive cover
8 . . . bank,
9 . . . plating,
10 . . . cut,
100 . . . pressure detection module,
111 . . . strip-shaped portion

The invention claimed is:

1. A method for manufacture of a pressure sensor, comprising:
forming a conductor pattern by means of a subtractive process in which a metal foil laminated through an adhesive agent on a surface of a base film is subjected to etching processing to provide a pair of electrodes on said base film;
laminating a photosensitive cover on said base film, and removing at least a portion of said conductor pattern corresponding to said pair of electrodes thereby to cause said portion to be exposed, while covering a remaining portion of said conductor pattern with a remaining portion of said photosensitive cover;
applying metal plating treatment for prevention of oxidation to the exposed portion of said conductor pattern including said pair of electrodes; and
forming, thereafter, a hollow portion opened to outside air in the removed portion of said photosensitive cover corresponding to said pair of electrodes, by laminating a cover film with a pressure sensing part formed thereon in advance in which contact resistance thereof changes according to a pressure of contact thereof with said electrodes, and by bonding said cover film to the remaining portion of said photosensitive cover by means of an adhesive agent.

2. The method for manufacture of a pressure sensor as set forth in claim 1, wherein
at the time of removing that portion of said photosensitive cover which corresponds to said electrode on said base film, said photosensitive cover is used to shape a spacer and a bank, and said cover film is bonded to said spacer, but non-bonded to said bank.

* * * * *